United States Patent [19]

Schnorrenberg et al.

[11] Patent Number: 5,710,155

[45] Date of Patent: Jan. 20, 1998

[54] ARYLGLYCINAMIDE DERIVATIVES, PROCESSES FOR THE MANUFACTURE THEREOF AND PHARMACEUTICAL COMPOSITIONS CONTAINING THESE COMPOUNDS

[75] Inventors: Gerd Schnorrenberg, Gau-Algesheim; Horst Dollinger; Franz Esser, both of Ingelheim am Rhein; Hans Briem, Budenheim; Birgit Jung, Bingen/Rhein; Georg Speck, Ingelheim am Rhein, all of Germany

[73] Assignee: Boehringer Ingelheim KG, Ingleheim am Rhein, Germany

[21] Appl. No.: 688,478

[22] Filed: Jul. 30, 1996

Related U.S. Application Data

[63] Continuation of Ser. No. 473,470, Jun. 7, 1995, abandoned.

[30] Foreign Application Priority Data

Apr. 14, 1995 [DE] Germany .......................... 195 14 112.1
May 25, 1995 [DE] Germany .......................... 195 19 245.1

[51] Int. Cl.$^6$ .......................... A61K 31/495; C07D 295/15
[52] U.S. Cl. .......................... 514/255; 544/130; 544/393; 544/400; 546/20; 546/118; 546/191; 546/194; 546/199; 546/208; 546/210; 546/224; 546/225; 546/234
[58] Field of Search .................... 544/393, 400; 514/235

[56] References Cited

U.S. PATENT DOCUMENTS 3,518,274  6/1970  Strycker .
3,862,946  1/1975  Havera .
3,906,100  9/1975  Havera .
5,434,158  7/1995  Shah .

FOREIGN PATENT DOCUMENTS

WO9401402   7/1993  WIPO .
WO9410146  11/1993  WIPO .
9408983   4/1994  WIPO .
WO9526335   3/1995  WIPO .
WO9608480   9/1995  WIPO .

OTHER PUBLICATIONS

*Chemical Abstracts*, vol. 68, No. 3, p. No. 5717, Abstract No. 59230g (1968).
*Chemical Abstracts*, vol. 11, No. 13, p. No. 7, Abstract No. 54228t (1972).
K. Nagarajan et al., "A Novel Displacement Reaction on a α-Chlorodiphenylacetamides", *Tetrahedron Letters*, 15, pp. 1387-1390)1967.

Primary Examiner—Robert W. Ramsuer
Attorney, Agent, or Firm—Robert P. Raymond; Alan R. Stempel; Mary-Ellen Devlin

[57] ABSTRACT

The invention relates to new arylglycinamide derivatives of general formula I

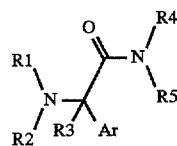

and the pharmaceutically acceptable salts thereof, wherein $R^1$, $R^2$, $R^3$, $R^4$, $R^5$ and Ar have the meanings given in the specification, and the preparation and use thereof. The new compounds are valuable neurokin (tachykinin) antagonists.

10 Claims, No Drawings

ARYLGLYCINAMIDE DERIVATIVES, PROCESSES FOR THE MANUFACTURE THEREOF AND PHARMACEUTICAL COMPOSITIONS CONTAINING THESE COMPOUNDS

This is a continuation of application Ser. No. 08/473,470, filed Jun. 7, 1995 now abandoned.

The invention relates to new arylglycinamide derivatives of general formula I

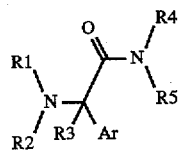
I and the pharmaceutically acceptable salts thereof, processes for preparing them and pharmaceutical compositions containing these compounds. The compounds are valuable neurokinin (tachykinin) antagonists.

The abbreviations used in the specification and claims are explained as follows:

CDI=Carbonyldiimidazole
DCCI=Dicyclohexylcarbodiimide
HOBt=1-Hydroxybenzotriazole
THF=Tetrahydrofuran
DMF=Dimethylformamide
RT=Room temperature
DMAP=4-Dimethylaminopyridine
TBTU=O-Benzotriazolyl-tetramethyluronium-tetrafluoroborate In order to show the formulae, a simplified representation is used. In the representation of the compounds all $CH_3$— substituents are represented by a single bond, and for example the following formula

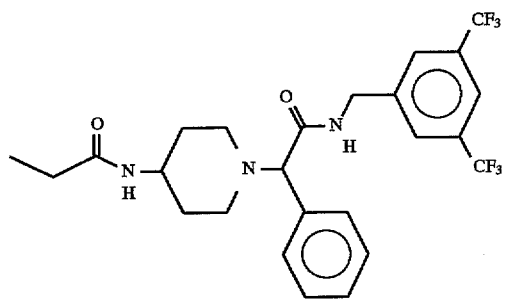

represents

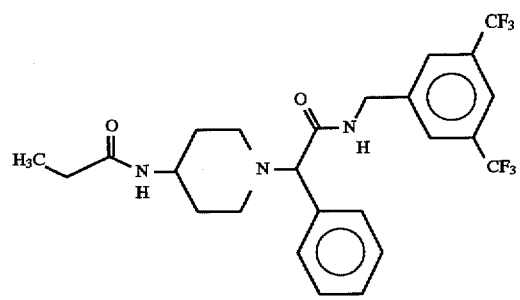

The invention relates to new arylglycinamide derivatives of general formula I

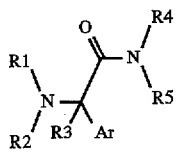
I or the pharmaceutically acceptable salts thereof, wherein

Ar denotes unsubstituted or mono- to penta-substituted phenyl, or unsubstituted or mono- or di-substituted naphthyl, in which the substituents of the phenyl and naphthyl independently of each other denote halogen (F, Cl, Br, I), $(C_{1-4})$alkyl, O-$(C_{1-4})$alkyl, $CF_3$, $OCF_3$ or $NR^9R^{10}$ (wherein $R^9$ and $R^{10}$ independently of each other denote H, methyl or acetyl);

$R^1$ and $R^2$ together with the N to which they are bound form a 6-membered ring of the formula

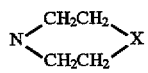

wherein

X denotes oxygen, $N(CH_2)_n R^6$ or $CR^7 R^8$, wherein n is 0, 1 or 2, $R^6$ is $(C_{3-7})$cycloalkyl, phenyl or naphthyl, wherein the phenyl may be mono- to tri-substituted by halogen (F, Cl, Br, I), $(C_{1-4})$alkyl, O-$(C_{1-4})$alkyl, $CF_3$, $OCF_3$ or $NR^9R^{10}$ (wherein $R^9$ and $R^{10}$ independently of each other denote H, methyl or acetyl);

$R^7$ and $R^8$ have one of the following meanings:

a) $R^7$ and $R^8$ represent H if $R^3$ is unsubstituted or substituted phenyl, b) $R^7$ is

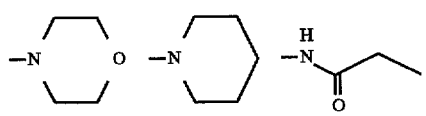

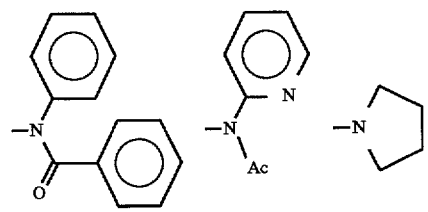

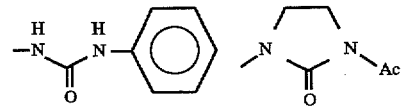

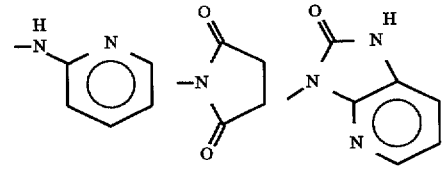

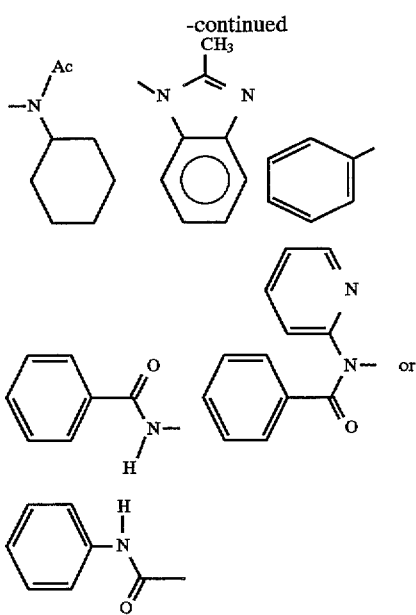

if R⁸ is H, —CONH₂, —NHC(O)CH₃ or —N(CH₃)C(O)CH₃,
or c) R⁷ and R⁸ together form the group

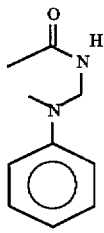

R³ denotes H, (C₁₋₄)alkyl, unsubstituted or mono- to tri-substituted phenyl, wherein the substituents independently of one another represent halogen (F, Cl, Br, I), (C₁₋₄)alkyl, O-(C₁₋₄)alkyl, CF₃, OCF₃ or NR⁹R¹⁰ (wherein R⁹ and R¹⁰ independently of one another denote H, methyl or acetyl);

R⁴ denotes (CH₂)ₘ phenyl or (CH₂)ₘ naphthyl, wherein m is 1, 2 or 3 and phenyl may be substituted by 1 to 3 substituents, wherein the substituents independently of one another are halogen (F, Cl, Br, I), (C₁₋₄)alkyl, O-(C₁₋₄)alkyl, CF₃, OCF₃ or NR⁹R¹⁰ (wherein R⁹ and R¹⁰ independently of one another denote H, methyl or acetyl);
and R⁵ denotes H, (C₁₋₄)alkyl, (C₃₋₆)cycloalkyl or CH₂COOH.

The compounds according to the invention are valuable neurokinin (tachykinin) antagonists which have both substance P-antagonism and also neurokinin A- or neurokinin B-antagonistic properties. They are useful for the treatment and prevention of neurokinin-mediated diseases.

Compounds of general formula I may contain acid groups, chiefly carboxyl groups, and/or basic groups such as, for example, amino functions. Compounds of general formula I may therefore be obtained either as internal salts, as salts with pharmaceutically acceptable inorganic acids such as hydrochloric acid, sulphuric acid, phosphoric acid or sulphonic acid or organic acids (such as, for example, maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as, for example, diethylamine, triethylamine or triethanolamine, etc.

The compounds according to the invention may occur as racemates but may also be obtained as pure enantiomers, i.e. in (R)- or (S)-form.

The preferred compounds of general formula I are those wherein X is N(CH₂)ₙR⁶, wherein n is 0, 1 or 2 and R⁶ denotes (C₃₋₆)cycloalkyl, preferably cyclohexyl;

wherein X is CR⁷R⁸, wherein

R⁷ is 1-piperidinyl, 1-pyrrolidinyl or 4-morpholinyl and R⁸=H or —CONH₂, wherein preferably R⁷ is 1-piperidinyl and R⁸ is H;

wherein R³ is H or methyl, preferably H;

wherein R⁴ is (CH₂)ₘ phenyl, wherein m is 1, 2 or 3 and phenyl is unsubstituted or up to tri-substituted, preferably wherein m is 1 or 2 and phenyl is di-substituented;

wherein R⁴ is (CH₂)₁₋₂phenyl, wherein the phenyl is substituted by 2 CF₃ groups which are preferably at positions 3 and 5;

wherein R⁵ represents H or (C₁₋₄)alkyl, preferably H or methyl;

wherein Ar denotes phenyl having 0, 1, 2 or 3 substituents, preferably unsubstituted phenyl.

The term naphthyl used above includes both 1-naphthyl and 2-naphthyl.

Test results for compounds according to the invention:

The receptor affinity for the NK₁-receptor (substance P-receptor) is determined on human lymphoblastoma cells (IM-9) with cloned NK₁-receptors, measuring the displacement of ¹²⁵I-labelled substance P. The K_i-values thus obtained demonstrate the efficacy of the compounds:

|  | K_i |
|---|---|
| Compound of Example 3: | 1.4 nM |
| Compound of Example 4: | 1.0 nM |
| Compound of Example 5: | 1.3 nM |
| Compound of Example 33: | 1.3 nM. |

The compounds according to the invention are valuable neurokinin (tachykinin) antagonists which have, in particular, NK₁-antagonism, but also NK₂- and NK₃-antagonistic properties.

The compounds according to the invention are valuable neurokinin (tachykinin) antagonists which have both substance P-antagonism and also neurokinin A- or neurokinin B-antagonistic properties. They are useful for the treatment and prevention of neurokinin-mediated diseases such as respiratory complaints, e.g. asthma, bronchitis, rhinitis, coughs or expectoration and inflammatory eye diseases such as conjunctivitis, inflammatory skin diseases such as dermatitis and urticaria, inflammatory intestinal complaints such as ulcerative colitis or Crohn's disease, other inflammatory diseases such as polyarthritis or osteoarthritis and pain (e.g. migraine) and gastrointestinal diseases such as irritable bowel and diarrhoea.

The invention therefore also relates to the use of the compounds according to the invention as remedies and pharmaceutical preparations which contain these compounds. They are preferably for use in humans. The compounds according to the invention may be administered by intravenous, subcutaneous, intramuscular, intraperitoneal or intranasal route or by inhalation, by transdermal route, if desired with the aid of iontophoresis or enhancers known from the literature, and by oral route.

For parenteral administration, the compounds of formula I or the physiologically acceptable salts thereof, optionally with conventional substances such as solubilisers, emulsifiers or other adjuvants, may be made into solution, suspension or emulsion. Suitable solvents include, for example, water, physiological saline solutions or alcohols, e.g. ethanol, propanediol or glycerol, sugar solutions such as glucose or mannitol solutions or a mixture of various solvents.

In addition, the compounds may be administered by means of implants, e.g. of polylactide, polyglycolide or polyhydroxybutyric acid or by means of intranasal preparations.

The compounds according to the invention may be prepared by generally known methods.

The compounds may be prepared in various ways. The two commonest methods are shown in the following plan:

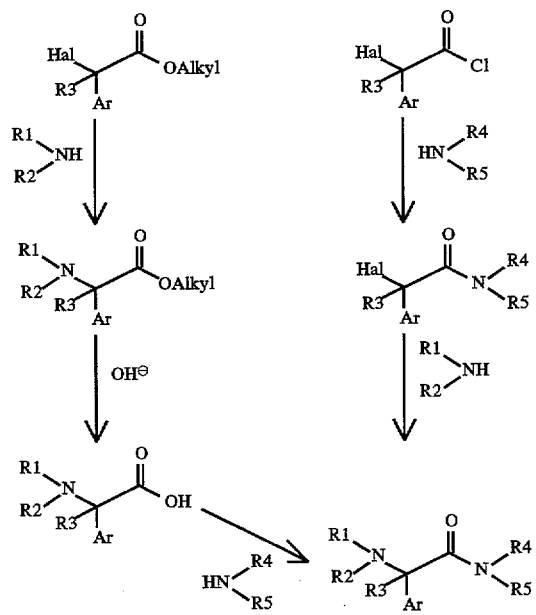

Method A

The carboxylic acid may be linked to the amine $HN(R^5)R^4$ in various ways. The usual methods are coupling methods such as those used in peptide chemistry. A coupling reagent such as TBTU, DCCI/HOBt, CDI, etc., is added to the coupling partners in an approximately equivalent amount. Suitable solvents are DMF, THF, $CH_2Cl_2$, $CHCl_3$, acetonitrile or other inert solvents or mixtures thereof. The appropriate temperature range is between $-50°$ C. and $+120°$ C., preferably between $0°$ C. and $40°$ C.

The carboxylic acid may also initially be converted by means of $SOCl_2$, $SO_2Cl_2$, $PCl_3$, $PCl_5$ or $PBr_3$ or mixtures thereof, by known methods, into the corresponding acid halide which is subsequently reacted with the amine $HN(R^5)R^4$ in an inert solvent such as $CH_2Cl_2$, THF or dioxane at temperatures between $-50°$ C. and $+100°$ C., typically between $0°$ C. and $20°$ C.

Another alternative is to convert the carboxylic acid initially into the alkylester, usually the methylester, by known methods and then to react this ester with the amine $HN(R^5)R^4$ in an inert solvent such as DMF, dioxane or THF. The reaction temperatures are between $20°$ C. and $150°$ C., typically between $50°$ C. and $120°$ C. The reaction may also be carried out in a pressurised container.

Process B

In this, the α-halo-arylacetamide derivative obtained according to known procedures is reacted with the amine $R^1(R^2)NH$, thereby generating hydrogen halide. In order to mop up the cleaved (or excess) hydrogen halide, inorganic bases are used such as $K_2CO_3$, $NaHCO_3$ or $CaCO_3$, or organic bases may be used such as triethylamine, Hünig base, pyridine or DMAP, or an excess of the amine $R^1(R^2)NH$ may be used. DMF, THF, dioxane or other inert solvents are used. The temperature range for the reaction is from $0°$ to $100°$ C., typically from $10°$ to $80°$ C.

Process C

The compounds according to the invention in which $R^5$ is not H may also be prepared as follows: first of all, the corresponding compound in which $R^5$ is H is synthesised according to process A or B. Then N-alkylation is carried out as follows in order to introduce alkyl, cycloalkyl or $CH_2COOH$. The compound according to the invention wherein $R^5$ is H is deprotonated with an equivalent quantity of NaH, $NaNH_2$, KOH, $NaOCH_3$ or some other strong base. Anhydrous inert solvents such as THF, dioxane or diethylether are used. Then the corresponding alkylating agent is added slowly in the form of the corresponding halide, rosylate or mesylate. The reaction is carried out in the temperature range from $-50°$ C. to $+100°$ C., typically between $0°$ C. and $+50°$ C. The method is described in detail in Example 33.

EXAMPLE 1

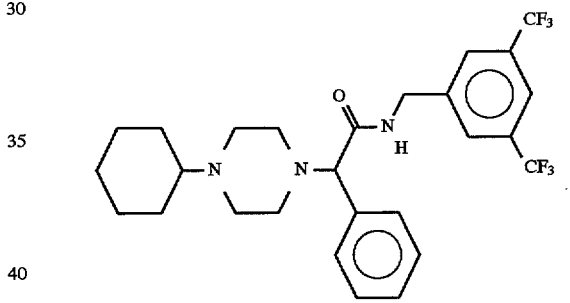

1st Step 2.2 g of 1-cyclohexylpiperazine were dissolved in 150 ml of anhydrous DMF, mixed with 2 g of $K_2CO_3$, stirred at RT and then cooled to $5°$ C. 2.7 g of methyl (R,S)-α-bromophenylacetic acid were added and the suspension was stirred overnight at RT. The precipitate was filtered off and the filtrate was evaporated down. The residue was taken up in ethyl acetate, extracted twice with 10% $KHCO_3$ solution and once with saturated NaCl solution. The organic phase was dried over $Na_2SO_4$, filtered and evaporated down, and 3.7 g of (R,S)-1-cyclohexyl-4-(methyl 2-phenylacetate)-piperazine were obtained in the form of a yellow oil. Yield: about 100%.

2nd Step 2.3 g of the product of the first step were dissolved in 10 ml of methanol, mixed with 14 ml of 1N NaOH and the resulting emulsion was stirred overnight at RT. The clear reaction solution was neutralised by the addition of 14 ml of 1N HCl, evaporated to dryness, the residue was treated with isopropanol and the solid matter was collected by suction filtration. The filtrate was evaporated down and the residue was triturated again with isopropanol, the solid matter was suction filtered and combined with the solid obtained earlier. In this way, 1.6 g of (R,S)-1-cyclohexyl-4-(2-phenylacetic acid)-piperazine were obtained as a white solid. Yield: 75%.

3rd Step 0.6 g of the product of the second step, 0.48 g of 3,5-bis-(trifluoromethyl)-benzylamine and 0.32 g of HOBT were suspended in 60 ml of THF/CH$_2$Cl$_2$ (1:1) and adjusted to pH 8.5 by the addition of about 0.7 ml of Hünig base. 0.77 g of TBTU were added and the mixture was stirred overnight at RT. The clear reaction solution was evaporated down in vacuo, the residue was taken up in CH$_2$Cl$_2$ and extracted twice with 10% KHSO$_4$ solution, once with saturated NaCl solution, twice with 10% KHCO$_3$ solution and once more with saturated NaCl solution. The organic phase was dried over Na$_2$SO$_4$, filtered off and evaporated down, whereupon crystallisation took place. 0.685 g of (R,S)-1-cyclohexyl-4-[2-phenylacetic acid-N-(3,5bis-trifluoromethylbenzyl) amide] were obtained as a yellowish solid. Yield 64%. Mp: 124°–129° C. FAB-MS: (M+H)$^+$=528.2.

EXAMPLE 2

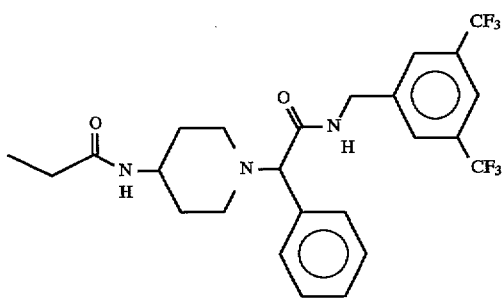

1st Step 0.49 g of 3,5-bis-(trifluoromethyl)-benzylamine were dissolved in 30 ml of anhydrous CH$_2$Cl$_2$, 0.3 ml of triethylamine were added, the mixture was cooled in an ice bath and over 20 minutes a solution of 0.46 g of (R,S)-a-bromophenylacetyl chloride in 10 ml of CH$_2$Cl$_2$ was added dropwise. After the mixture had stood at RT over a weekend, the solvent was eliminated and the solid residue was triturated with diethylether, suction filtered and the filtrate was evaporated down. 0.6 g of α-bromophenylacetic acid N-(bis-trifluoromethyl-benzyl)-amide were obtained as a light beige solid. Yield: 43.5%.

2nd Step 0.21 g of 4-propionylamino-piperidine hydrochloride were dissolved in 30 ml of anhydrous DMF, 0.33 g of K$_2$CO$_3$ were added and the mixture was stirred for 30 minutes at room temperature. Over 20 minutes a solution of 0.68 g of the product of the first step in 10 ml of DMF were added dropwise to this mixture, which was then stirred overnight at room temperature. The suspension was filtered, the filtrate was evaporated down, the oily residue obtained was taken up in ethyl acetate, extracted twice with 10% KHCO$_3$ solution and once with saturated NaCl solution. The organic phase was dried over Na$_2$SO$_4$, filtered, the filtrate was evaporated down and the semi-solid residue obtained was triturated with diethylether and suction filtered. 0.33 g of (R,S)-4-propionylamino-1-[2phenylacetic acid-N(3,5-bis-trifluoromethyl-benzyl)-amide]-piperidine were obtained as a white solid. Yield: 64%. Mp: 189°–191° C. FAB-MS: (M+H)$^+$=516.4.

EXAMPLE 33

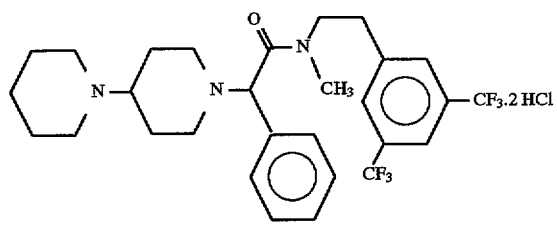

0.3 g of the compound according to Example 25 were converted into the corresponding base by treatment with KHCO$_3$ and dried. The resulting product was dissolved in 5 ml of anhydrous THF, 34 mg of NaH (60% in oil) were added and the mixture was stirred for 1.5 hours at RT. Then 0.1 g of methyliodide were added and the mixture was stirred overnight. The reaction mixture was mixed with 2 ml of THF/water (1:1) then with 25 ml of water and extracted 3 times with ether. The combined ether extracts were dried over Na$_2$SO$_4$ and evaporated down in vacuo, thereby obtained 170 mg of the desired compound in the form of a free base (oil). This was converted into the dihydrochloride by the addition of an excess of ethereal HCl, the dihydrochloride being obtained in the form of yellow crystals. Yield: 113 mg (36%). Mp: >240° C.; FAB-MS: (M+H)$^+$=556.4

The other compounds of the invention may be prepared analogously, e.g. as follows:

EXAMPLE 3

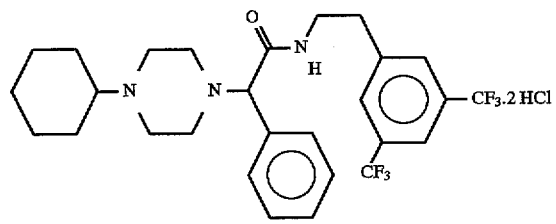

Mp: 235°–238° C. FAB-MS: (M+H)$^+$=542.2.

EXAMPLE 4

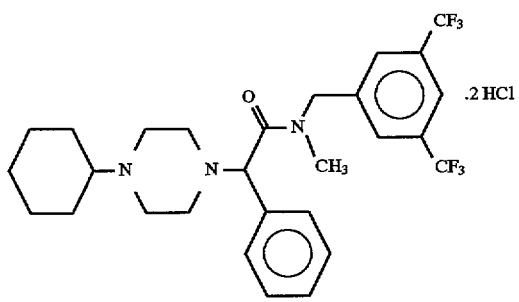

Mp: >240° C. (Decomp.). FAB-MS: (M+H)$^+$=542.3.

EXAMPLE 5
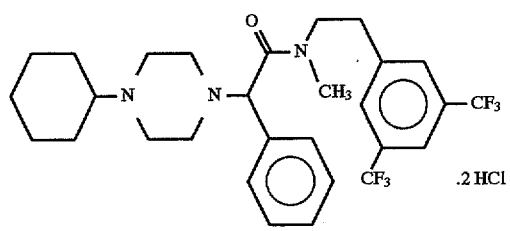
Mp: 158°–164° C.; FAB-MS: (M+H)$^+$=556.4.
EXAMPLE 6
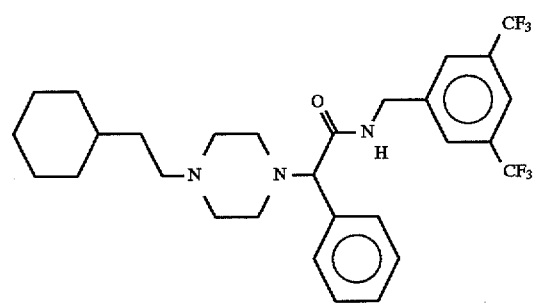
Mp: 97°–99° C.; FAB-MS: (M+H)$^+$=556.3.
EXAMPLE 7
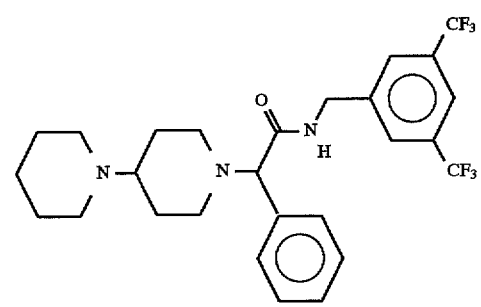
Mp: >240° (Decomp.); FAB-MS: (M+H)$^+$=528.4.
EXAMPLE 8
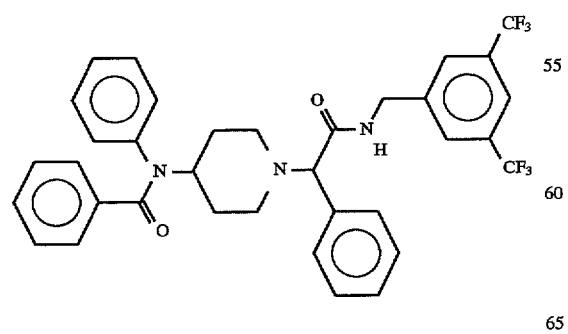
Mp: 102°–105° C.; FAB-MS: (M+H)$^+$=640.3.
EXAMPLE 9
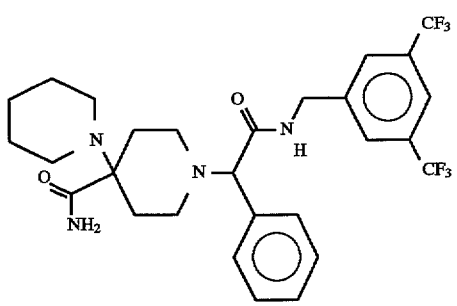
Mp: 141°–149° C.; FAB-MS: (M+H)$^+$=579.2.
EXAMPLE 10
Mp: 218°–223° C.; FAB-MS: (M+H)$^+$=579.3.
EXAMPLE 11
Mp: >220° (Decomp.); FAB-MS (M+H)$^+$=571.3.
EXAMPLE 12
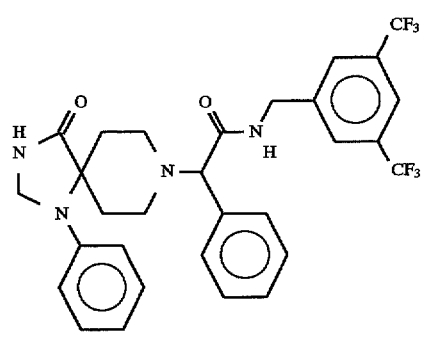
Mp: 205°–210° C.; FAB-MS: (M+H)$^+$=591.3.

EXAMPLE 13
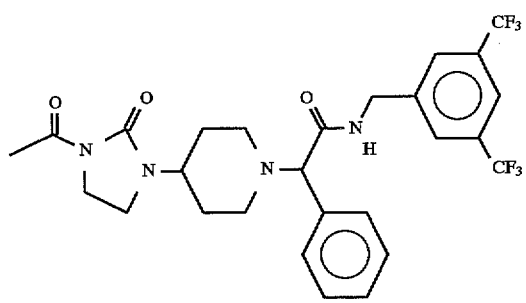
Mp: 87°–95° C.; FAB-MS: (M+H)$^+$=571.2
EXAMPLE 14
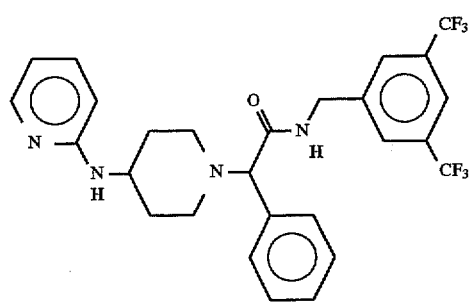
Mp: 164°–166° C.; FAB-MS: (M+H)$^+$=537.3.
EXAMPLE 15
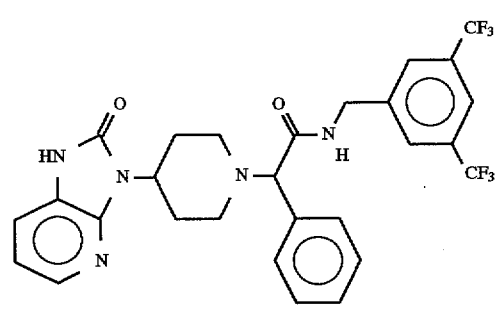
Mp: 208°–210° C.; FAB-MS: (M+H)$^+$=578.3.
EXAMPLE 16
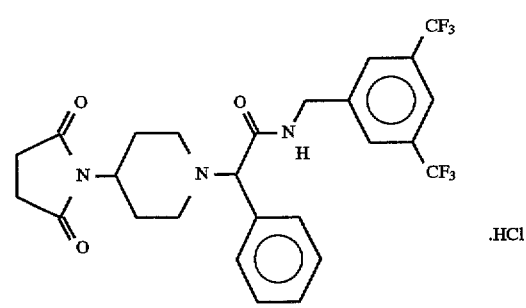
.HCl
Mp: 110°–115° C.; FAB-MS: (M+H)$^+$=542.3.
EXAMPLE 17
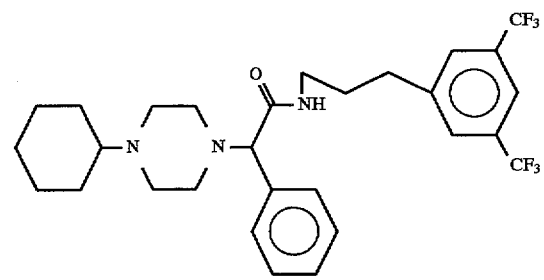
Mp: 118°–123° C.; FAB-MS: (M+H)$^+$=556.3
EXAMPLE 18
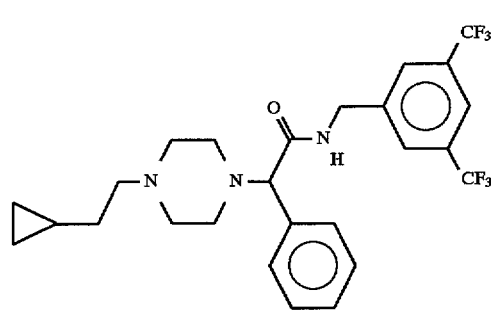
Mp: 134°–136° C.; FAB-MS: (M+H)$^+$=514.3
EXAMPLE 19
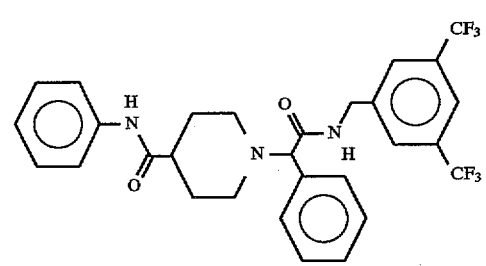
Mp: >240° (Decomp.): FAB-MS: (M+H)$^+$=564
EXAMPLE 20
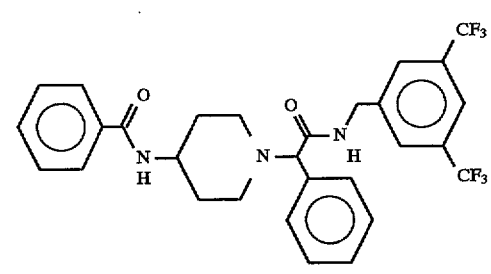
Mp: 180°–185° C.; FAB-MS: (M+H)$^+$=564.3

EXAMPLE 21
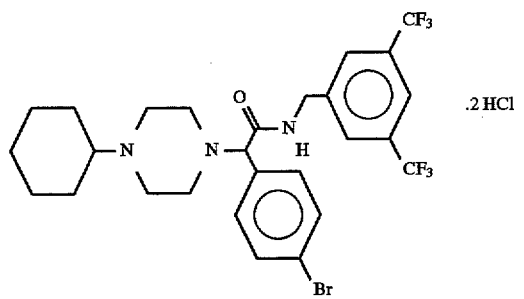
Mp: 228°–232° C.; FAB-MS: (M+H)⁺=606/608
EXAMPLE 22
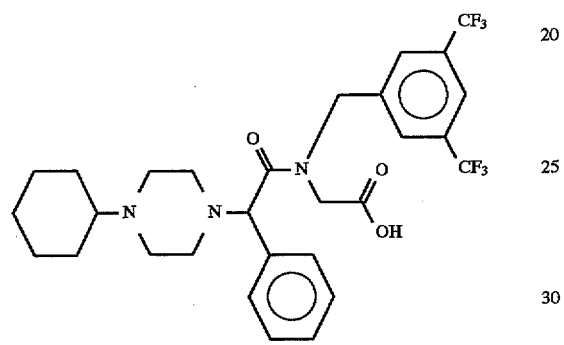
Mp: 70°–73° C.; FAB-MS: (M+H)⁺=586
EXAMPLE 23
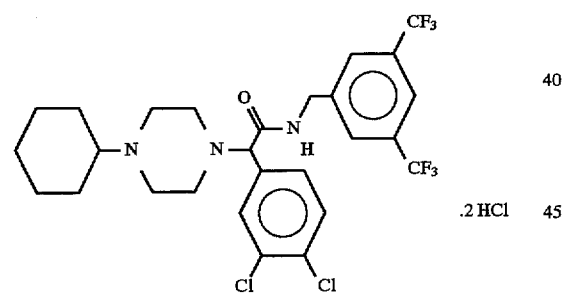
Mp: 248°–254° C.; FAB-MS: (M+H)⁺=596/598/600
EXAMPLE 24
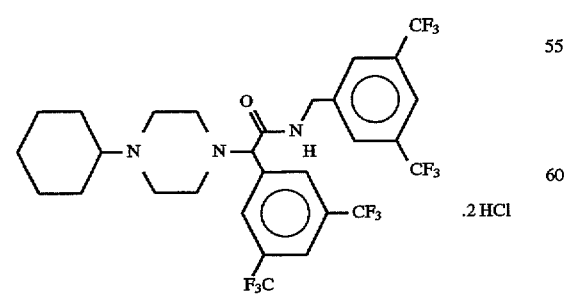
Mp: 210° C.; FAB-MS: (M+H)⁺=664.1
EXAMPLE 25
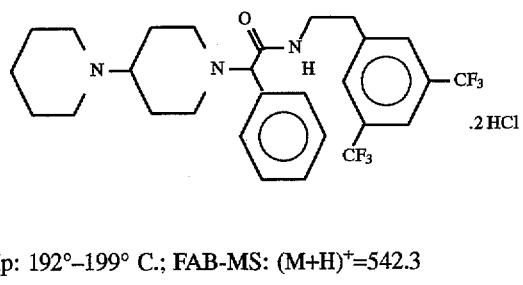
Mp: 192°–199° C.; FAB-MS: (M+H)⁺=542.3
EXAMPLE 26
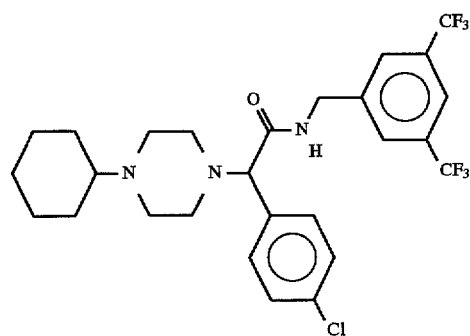
Mp: 112°–118° C.; FAB-MS: (M+H)⁺=562/564
EXAMPLE 27
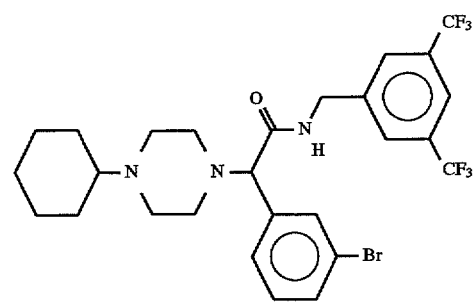
Mp: 124°–127° C.; FAB-MS: (M+H)⁺=606/608
EXAMPLE 28
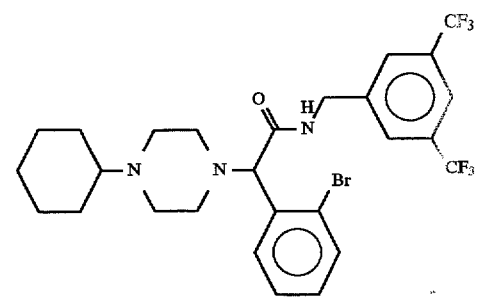
Mp: 118°–120° C.; FAB-MS: (M+H)⁺=606/608

EXAMPLE 29
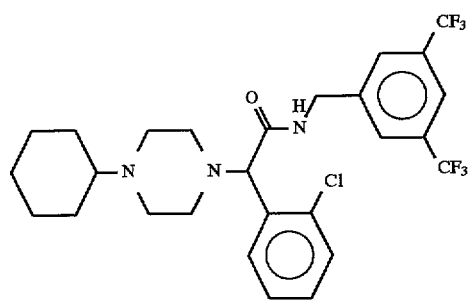
Mp: 120°–122° C.; FAB-MS: (M+H)⁺=562/564
EXAMPLE 30
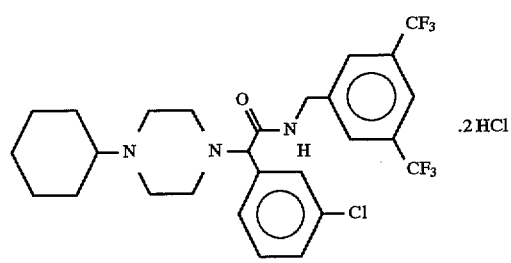
Mp: >240° C.; FAB-MS: (M+H)⁺=562/564
EXAMPLE 31
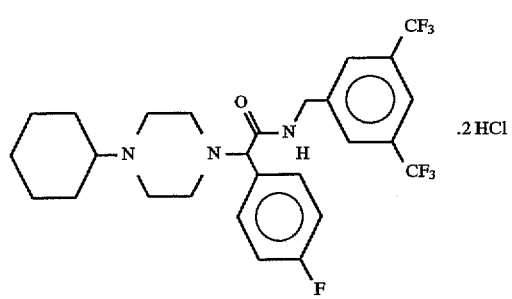
Mp: >240° C.; FAB-MS: (M+H)⁺=546.3
EXAMPLE 32
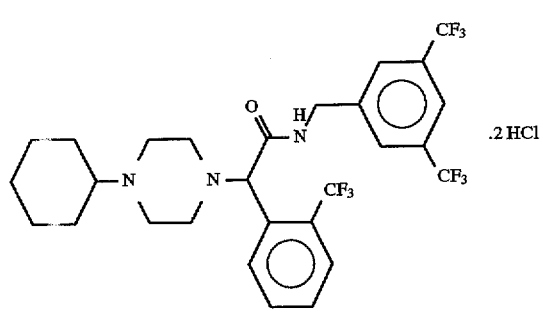
Mp: 125°–130° C. (Decomp.); FAB-MS: (M+H)⁺=610.4
EXAMPLE 34
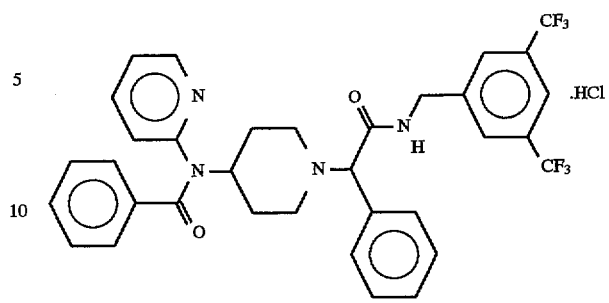
Mp: 145°–151° C.; FAB-MS: (M+H)⁺=641.3
EXAMPLE 35
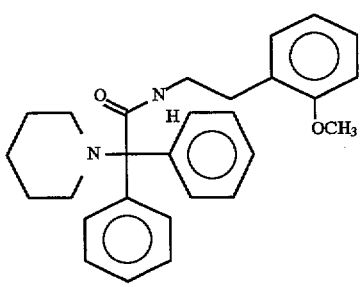
EXAMPLE 36
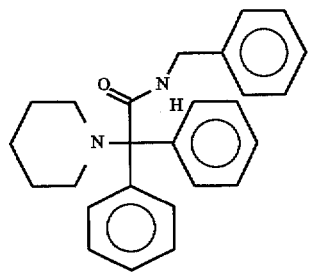
Mp: 175°–176.5° C.
EXAMPLE 37
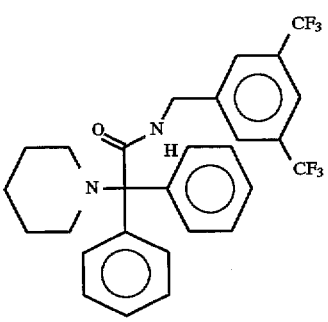
Mp: 157°–158° C.

EXAMPLE 38
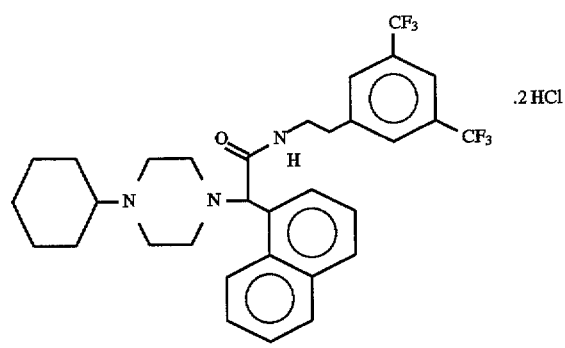
Mp: 155°–172° C. FAB-MS: (M+H)+=592.2
EXAMPLE 39
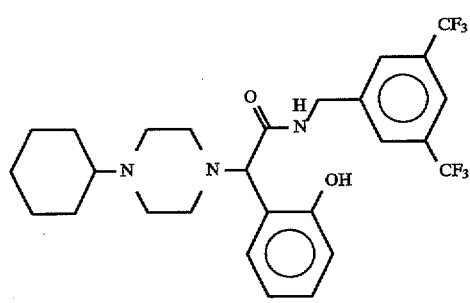
EXAMPLE 40
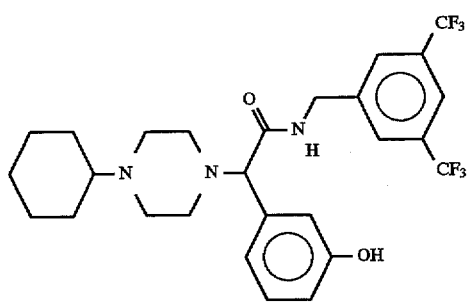
EXAMPLE 41
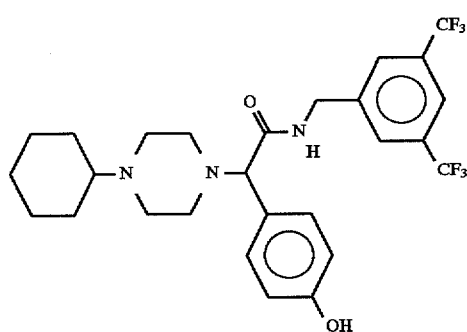
EXAMPLE 42
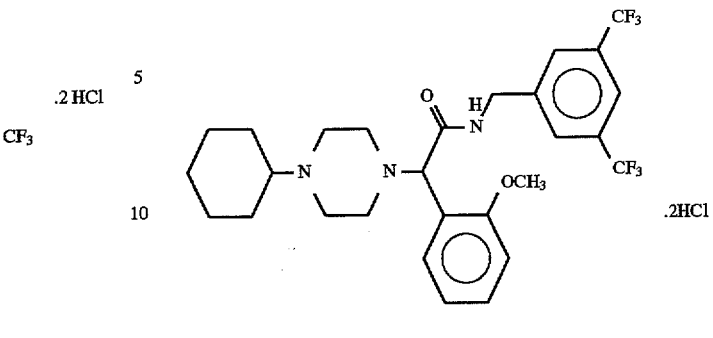
Mp: 142°–150° C. FAB-MS: (M+H)+=558.2
EXAMPLE 43
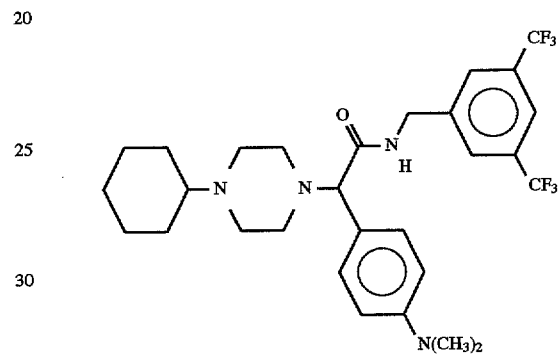
EXAMPLE 44
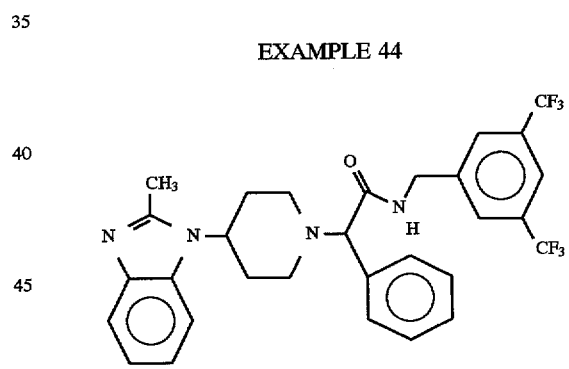
Mp: 107°–111° C.; FAB-MS: (M+H)+=575.6
EXAMPLE 45
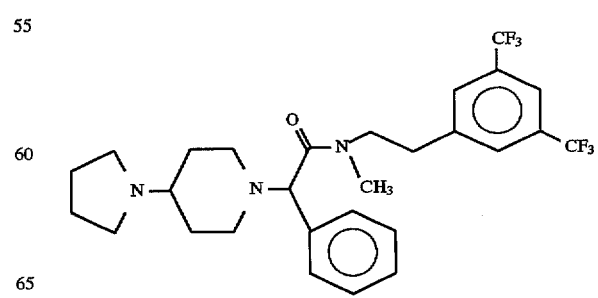

EXAMPLE 46
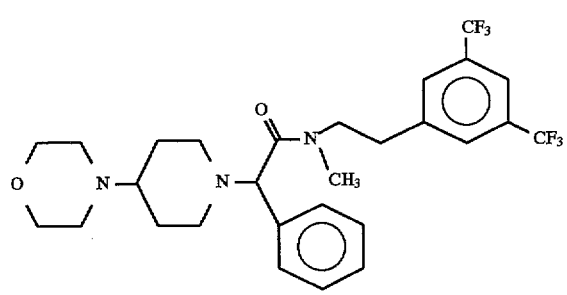
EXAMPLE 47
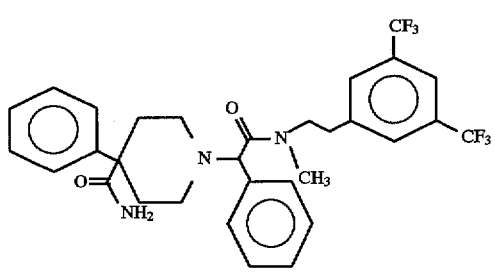
EXAMPLE 48
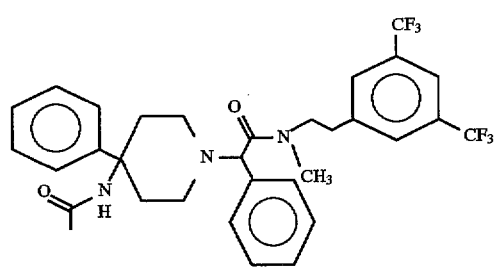
EXAMPLE 49
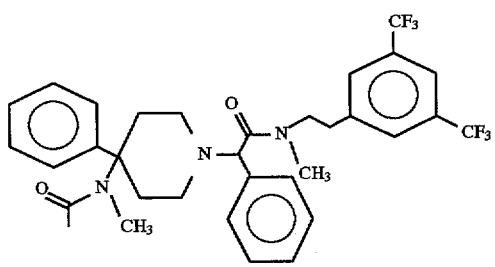
EXAMPLE 50
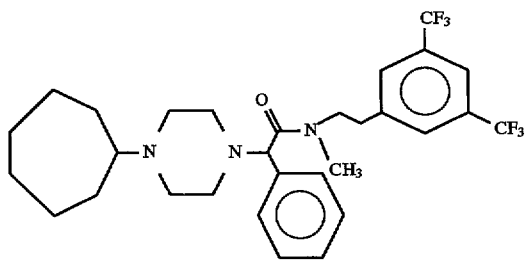
EXAMPLE 51
EXAMPLE 52
Mp: 133°–143° C.
EXAMPLE 53

EXAMPLE 54
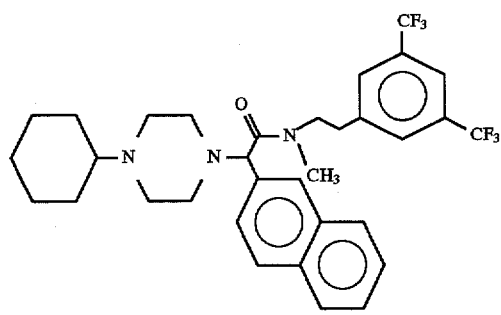
EXAMPLE 55
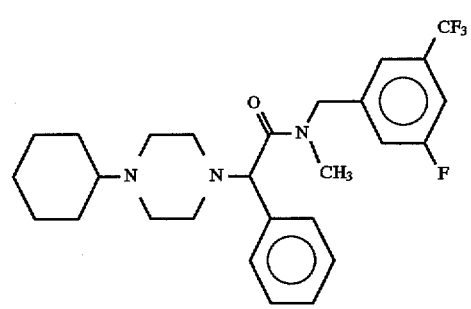
EXAMPLE 56
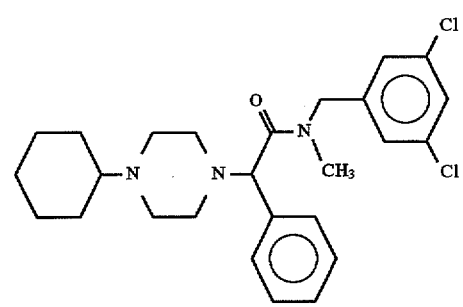
EXAMPLE 57
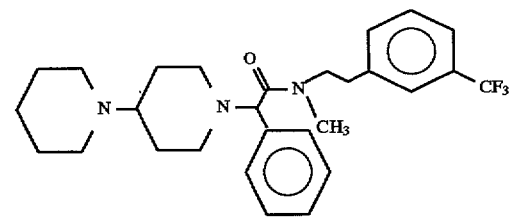
EXAMPLE 58
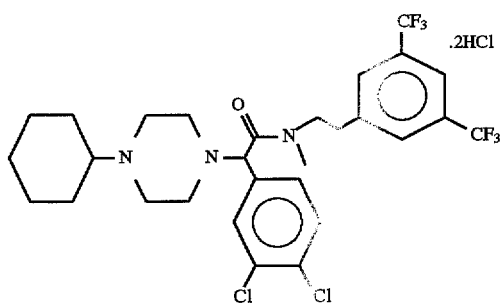
Mp: 212°–216° C. (Decomp.)
EXAMPLE 59
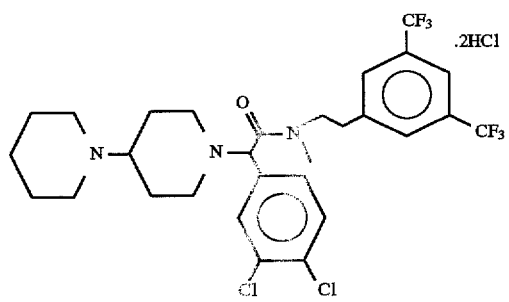
Mp: 244°–246° C. (Decomp.) FAB-MS: (M+H)$^+$=624.1/ 626.2/628
EXAMPLE 60
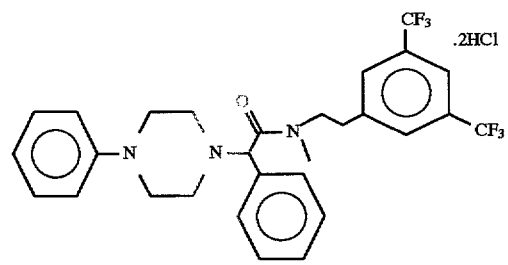
Mp: 113°–123° C.
EXAMPLE 61
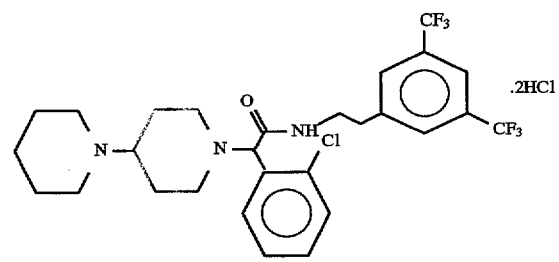
Mp: 195°–205° C.

EXAMPLE 62

Mp: 210°–218° C. FAB-MS: (M+H)⁺=620/622

EXAMPLE 63

Mp: 215°–224° C. FAB-MS: (M+H)⁺=576/578

EXAMPLE 64

Mp: 85°–92° C. FAB-MS: (M+H)⁺=572.5

Pharmaceutical Preparations:

Injectable solution 200 mg of active substance*
1.2 mg of monopotassium dihydrogen phosphate = KH$_2$PO$_4$ } (buffer)
0.2 mg of disodium hydrogen phosphate = NaH$_2$PO$_4$.2H$_2$O
94 mg of sodium chloride or } (isotonic)
520 mg of glucose
4 mg of albumin (protease protection)
q.s. sodium hydroxide solution } to adjust the pH
q.s. hydrochloric acid
to pH 6
sufficient water to make a
10 ml solution for injection Pharmaceutical Preparations:

Injectable solution 200 mg of active substance*
94 mg of sodium chloride
or
520 mg of glucose
4 mg of albumin
q.s. sodium hydroxide solution } to adjust the pH
q.s. hydrochloric acid
to pH 9
sufficient water to make a
10 ml solution for injections Lyophilisate 200 mg of active substance*
520 mg of mannitol (isotonic/structural component)
4 mg of albumin
Solvent 1 for lyophilisate
10 ml of water for injections
Solvent 2 for lyophilisate
20 mg of Polysorbate ® 80 = Tween ® 80 (surfactant)
10 ml of water for injections

*Active substance: compounds according to the invention, e.g. those of any one of Examples 1 to 64.

Dosage for humans weighing 67 kg: 1 to 500 mg

What is claimed is:
1. An arylglycinamide derivative of the formula I or the pharmaceutically acceptable salts thereof, wherein
Ar denotes unsubstituted or mono- to penta-substituted phenyl, or unsubstituted or mono- or di-substituted naphthyl, in which the substituents of the phenyl and naphthyl independently of each other denote halogen (F, Cl, Br, I), (C$_{1-4}$)alkyl, O-(C$_{1-4}$)alkyl, CF$_3$, OCF$_3$ or NR$^9$R$^{10}$ (wherein R$^9$ and R$^{10}$ independently of each other denote H, methyl or acetyl);

R$^1$ and R$^2$ together with the N to which they are bound form a 6-membered ring of the formula $$N\underset{CH_2CH_2}{\overset{CH_2CH_2}{<}}X$$

wherein
X denotes N(CH$_2$)$_n$R$^6$;
N is 0, 1 or 2,
R$^6$ is (C$_{3-7}$)cycloalkyl, phenyl or naphthyl, wherein the phenyl may be mono- to tri-substituted by halogen (F, Cl, Br, I), (C$_{1-4}$)alkyl, O-(C$_{1-4}$)alkyl, CF$_3$, OCF$_3$ or NR$^9$R$^{10}$ (wherein R$^9$ and R$^{10}$ independently of each other denote H, methyl or acetyl);

R$^3$ denotes H, (C$_{1-4}$)alkyl, unsubstituted or mono- to tri-substituted phenyl, wherein the substituents independently of one another represent halogen (F, Cl, Br, I), (C$_{1-4}$)alkyl, O-(C$_{1-4}$)alkyl, CF$_3$, OCF$_3$ or NR$^9$R$^{10}$ (wherein R$^9$ and R$^{10}$ independently of one another denote H, methyl or acetyl);

R$^4$ denotes (CH$_2$)$_m$ phenyl or (CH$_2$)$_m$ naphthyl, wherein m is 1, 2 or 3 and phenyl may be substituted by 1 to 3 substituents, wherein the substituents independently of one another are halogen (F, Cl, Br, I), $(C_{1-4})$alkyl, O-$(C_{1-4})$alkyl, $CF_3$, $OCF_3$ or $NR^9R^{10}$ (wherein $R^9$ and $R^{10}$ independently of one another denote H, methyl or acetyl);

$R^5$ denotes H, $(C_{1-4})$alkyl, $(C_{3-6})$cycloalkyl or $CH_2COOH$.

2. A compound according to claim 1, wherein n is 0, 1 or 2 and $R^6$ is $(C_{3-6})$cycloalkyl.

3. A compound according to claim 1, wherein $R^3$ is H or methyl.

4. A compound according to claim 1, wherein $R^4$ is $(CH_2)_m$phenyl, wherein m is 1, 2 or 3 and phenyl is unsubstituted or up to tri-substituted.

5. A compound according to claim 4, wherein $R^4$ is $(CH_2)_{1-2}$phenyl, wherein the phenyl is substituted by 2 $CF_3$ groups.

6. A compound according to claim 1, wherein $R^5$ denotes H or $(C_{1-4})$alkyl.

7. A compounds according to claim 1, wherein Ar denotes phenyl having 0, 1, 2 or 3 substituents.

8. A pharmaceutical preparation comprising a compound according to claim 1.

9. A method for treating a neurokinin-mediated disease which comprises administering to a host suffering from such condition a therapeutically effective amount of a compound according to claim 1.

10. A process for preparing the compounds of formula I according to claim 1, comprising the step of reacting an acid of formula

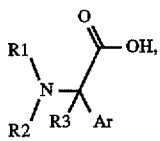

or the halide or alkylester thereof, with an amine of formula

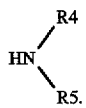

* * * * *